United States Patent [19]

Schwartz

[11] 4,455,374
[45] * Jun. 19, 1984

[54] SOLAR FERMENTATION AND DISTILLATION PROCESS

[76] Inventor: David M. Schwartz, 2400 E. 13th Ave., Denver, Colo. 80206

[*] Notice: The portion of the term of this patent subsequent to Feb. 8, 2000 has been disclaimed.

[21] Appl. No.: 398,210

[22] Filed: Jul. 14, 1982

Related U.S. Application Data

[63] Continuation-in-part of Ser. No. 149,903, May 15, 1980, abandoned, and Ser. No. 93,002, Nov. 9, 1979, Pat. No. 4,372,291.

[51] Int. Cl.³ .............................. C12P 7/06; F24J 3/02
[52] U.S. Cl. .................................... 435/161; 435/287; 126/443; 126/417; 126/438; 126/442; 126/452; 203/19; 203/90; 203/DIG. 1; 203/DIG. 13; 202/234; 202/236
[58] Field of Search ............... 435/161, 162, 163, 164, 435/165, 287; 426/494; 202/234, 236; 203/19, 90, DIG. 1, DIG. 13; 126/443, 438, 417, 432, 442, 435, 452

[56] References Cited

U.S. PATENT DOCUMENTS

| | | | |
|---|---|---|---|
| 102,633 | 5/1870 | Wheeler et al. | 203/DIG. 13 |
| 1,068,650 | 7/1913 | Harrison | 126/442 |
| 1,510,195 | 9/1924 | Römer | 435/164 |
| 2,205,378 | 6/1940 | Abbot | 126/443 |
| 2,490,659 | 12/1949 | Snyder | 126/432 |
| 3,236,740 | 2/1966 | Smith et al. | 435/161 |
| 3,390,672 | 7/1968 | Snelling | 126/443 |
| 3,940,492 | 2/1976 | Ehnstrom | 435/813 |
| 4,092,979 | 6/1978 | Kotlarz | 126/438 |
| 4,111,187 | 9/1978 | Wiegand | 126/432 |
| 4,124,020 | 11/1978 | Noble | 126/901 |
| 4,153,042 | 5/1979 | Tragert | 126/443 |
| 4,186,724 | 2/1980 | Nelson | 126/438 |
| 4,239,033 | 12/1980 | Matkouits | 126/438 |
| 4,372,291 | 2/1983 | Schwartz | 126/417 |

Primary Examiner—Thomas G. Wiseman
Assistant Examiner—John Tarcza
Attorney, Agent, or Firm—Wolf, Greenfield & Sacks

[57] ABSTRACT

A solar fermentation process and distillation system for the manufacture of ethanol product suitable for blending with motor gasoline or as a substitute fuel for gasoline. Fermentation of starches or sugars is carried out in situ in solar collector tubes. The raw beer product emanating from the solar tubes is purified into a high quality ethanol fuel product by passing the beer product through a series of distillation columns whose internal reboil vapor is generated in whole or in substantial part through direct application of solar heat energy. The use of solar energy as heating source in the fermentation and distillation steps markedly reduces the need for external utilities such as steam and fuel to run the plant thereby greatly reducing the operating costs of the plant.

3 Claims, 4 Drawing Figures

SOLAR FERMENTATION AND DISTILLATION PROCESS

BACKGROUND OF THE INVENTION

This application is a continuation-in-part of application Ser. No. 149,903 filed May 15, 1980, abandon and of application Ser. No. 93,002 filed Nov. 9, 1979, U.S. Pat. No. 4,372,291.

FIELD OF THE INVENTION

The present invention relates to a fermentation process and system for production of fuel grade ethanol utilizing solar energy to supply heat directly to the fermentation and purification steps within the process.

DESCRIPTION OF THE PRIOR ART

In prior art processes for the production and manufacture of high purity ethanol product through fermentation of starches and sugars the fermentation step is normally carried out in large closed vats wherein a raw ethanol beer-product of essentially uniform composition is produced within each vat. The reaction temperature is regulated by indirect heat exchangers in process communication with the vat or by electricity, fuel fired boilers or other external utility heat sources. Ultraviolet light has been used to augment the fermentation reaction rate in batch fermentation vats as disclosed in U.S. Pat. No. 1,140,882. Typically, the raw fermentation beer product emanating from the fermentation vats is purified in fractional distillation columns in two or three or more stages. Conventional distillation systems for the purification of the raw fermentation beer to produce high quality ethanol utilize either steam or other external utilities to generate heat needed to produce the reboil vapor within the distillation columns in order to make these columns functional. A 95% fuel grade ethanol product sufficiently free of volatile fusel oils, solids and other impurities resulting in a fuel product suitable for blending with gasoline can be produced in this manner in conventional distillation systems located downstream of the fermentation vats. However, although such prior art systems are feasible, the operating utility costs for this type of plant have been prohibitive in relation to the value of the fuel grade ethanol produced. Applicant by carrying out the fermentation in situ within solar collector tubes and utilizing solar energy as heating source in the fermentation and distillation steps have markedly reduced the need for external utilities such as steam, and fuel to run the plant. As a result, applicants have overcome the operating cost obstacles inherent in the prior art fermentation process systems for the manufacture of fuel grade ethanol.

SUMMARY OF THE INVENTION

It is an object of the present invention to provide a continual fermentation process and ethanol recovery system utilizing solar energy as a heat source for production of fuel grade ethanol for use as a substitute for gasoline or for blending with gasoline.

It is an important object of the invention to carry out the fermentation of starches or sugars in situ in solar collector tubes, the heat required to maintain the fermentation mixture at reaction temperature being supplied by sunlight energy.

It is another object of the invention to carry out the purification of the raw ethanol fermentation product in a series of fractionation columns whose internal reboil vapors are generated in whole or in part by sunlight heat energy.

The system of the invention comprises a feed pretreatment section, a solar fermentation section and distillation section. Fermentation for the production of fuel grade alcohol is carried out in a continual process by preparing a fermentation mixture of grain mash or sugar solution and yeast in the feed pretreatment section and by passing the fermentation solution through a series of solar collector tubes in the solar fermentation section of the process. The fermentation is carried out in situ as the fermentation mixture is passed through the solar collector tubes. The fermentation mixture is brought to and maintained at reaction temperature by sunlight heat energy supplied to the solar collector tubes. As the fermentation mixture passes through the solar tubes the mixture becomes increasingly richer in ethanol as fermentation occurs within the tubes. The fermented mixture emanating from the tubes is a raw ethanol mixture.

The raw ethanol product emanating from the solar collector tubes is purified within the distillation section of the process in a plurality of stages, preferably at least two stages comprised of a series of fractional distillation columns whose internal reboil vapors are generated in whole or in substantial part through heat supplied from sunlight energy thereby reducing the utility operating costs. From 50% to 100% of the reboil heat required in each distillation column can be supplied directly by sunlight heat energy. Alternatively the raw ethanol emanating from the solar fermentation section can be purified in conventional distillation equipment utilizing steam or external utility sources to supply the necessary reboiler heat to the distillation columns. Alternatively one or more of the distillation columns may be operated in conventional manner utilizing steam or external utilities to generate the required reboil vapor therein and one or more other distillation columns may utilize direct solar energy in whole or in substantial part, e.g. from 50% to 100% to generate the required reboil vapor therein. The process of the invention includes a heat recovery unit within the distillation section for reclaiming heat for use during night operation by condensing hot steam by-product from the distillation columns. The condensed steam is recycled to the feed pretreatment section of the process.

The process and system of the invention produces a 92% ethanol product containing no more than about 3% hydrocarbon impurities and no more than about 4 wt. % water and less than about 1% solids. This ethanol product may be blended with motor gasoline or used as a fuel substitute for gasoline.

DESCRIPTION OF THE PREFERRED EMBODIMENT

Figure 1:
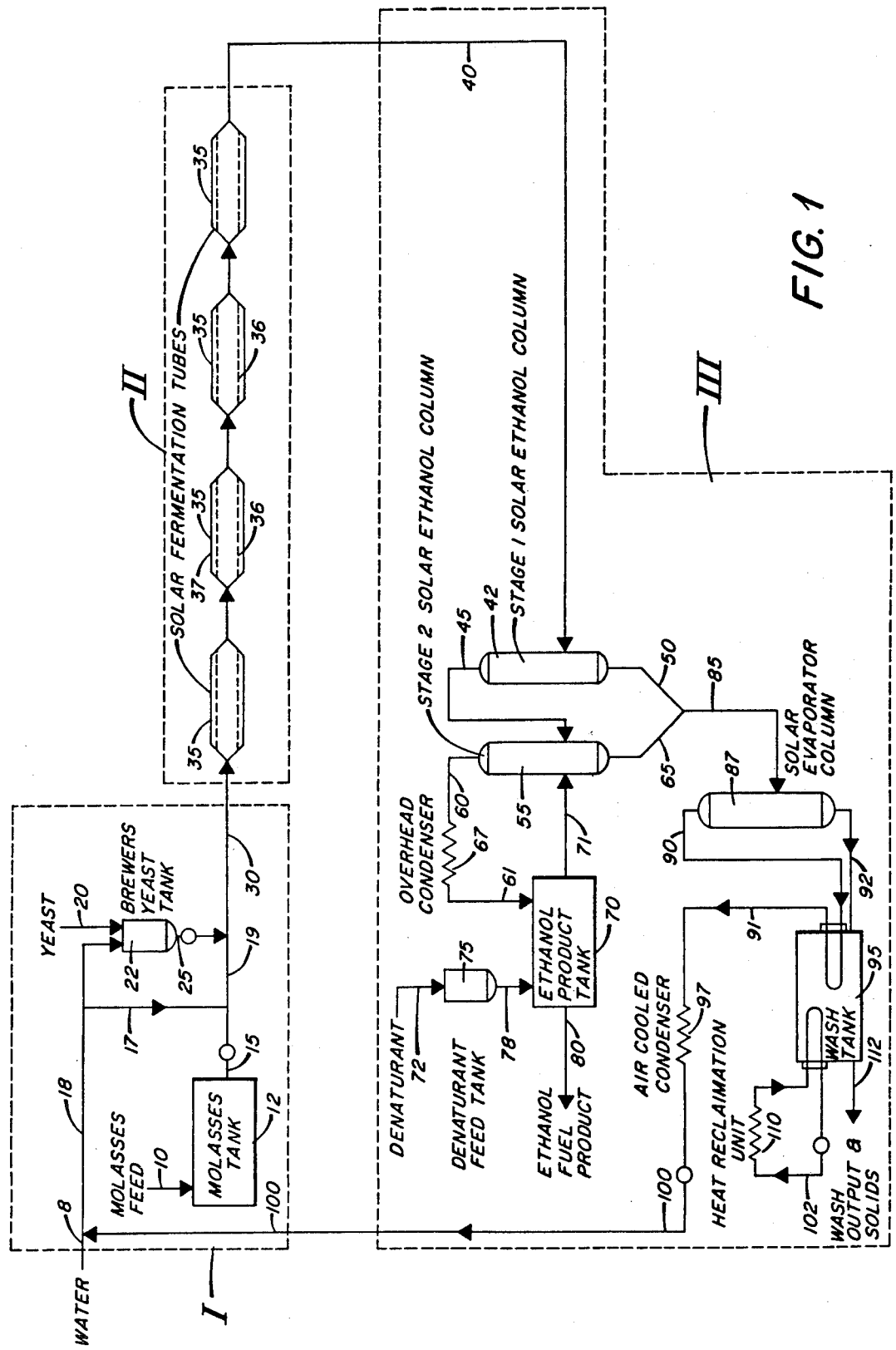
FIG. 1 is a schematic process flow diagram of one embodiment of the invention utilizing molasses feed.

A preferred embodiment of the invention utilizing molasses as feed is disclosed in FIG. 1. The process of the invention is comprised of a Feed Pretreatment Section I, a Solar Fermentation Section II, and a Distillation Section III.

Molasses, preferably at least 48% sugars molasses (i.e. blackstrap) is supplied to molasses tank 12 in the Feed Pretreatment Section I through feed line 10. The molasses is removed from the tank through line 15 and is admixed with water supplied through line 17 which is connected to water supply line 8. A line 19 is provided to carry the molasses water solution for admixture with yeast supplied downstream. A portion of the water entering through line 8 is diverted to line 18 and passes to brewer's yeast solution tank 22. Yeast is supplied to tank 22 through line 20. The yeast and water is admixed in tank 22 to form a yeast solution which passes from the tank through line 25. The yeast solution passes from line 25 and is admixed with the water and molasses passing through line 19.

Figure 4:
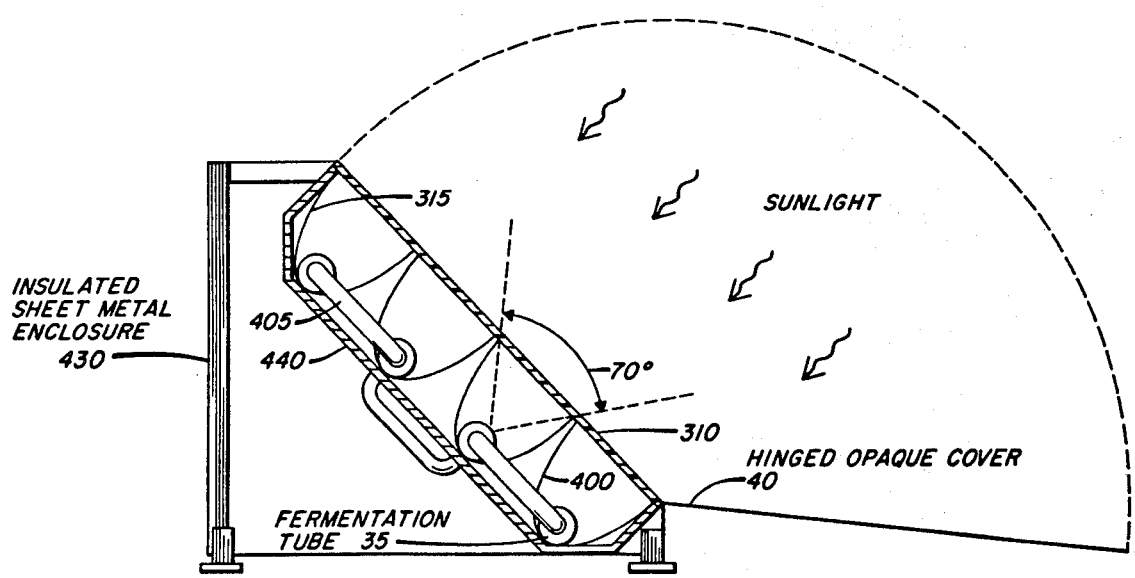
FIG. 4 is an elevational view of the solar fermentation tubes.

The molasses water and yeast mixture comprises a fermentation mixture which is pumped to solar heated fermentation tubes 35 of the Solar Fermentation Section II. The solar tubes 35 are tubes comprised of an inner metal pipe 36 and outer glass or clear plastic envelope 37 having an annular region between the metal tube and glass envelope evacuated to a pressure of about $10^{-6}$ torr such as that disclosed in U.S. Pat. No. 4,186,725. The metal tube is constructed preferably of stainless steel coated with a suitable heat absorption coating such a black tungston or black chrome on nickel. Parabolic reflectors 400 as best shown in FIG. 4 may be provided around the tube to enhance the rate of solar heat transfer to the tubes. The tubes may be arranged typically on a flat land surface having good exposure to sunlight. The molasses and yeast water solution passes through the metal inner tube 36 of the solar collector. A function of the solar fermentation tube of the invention is to heat the fermentation mixture to the precise fermentation reaction temperature required and permit fermentaion to occur as the mixture passes through the tubes. Therefore, as the fermentation mixture passes through the solar tubes, it becomes increasingly richer in ethanol along the length of the tubes. Thus an ethanol gradient of increasing ethanol concentration is developed along the length of the solar collector tubes in the direction of the mixture flow through the tubes. The temperature may be precisely regulated by adjusting the amount of the tube glass surface which is exposed to the sunlight through the use of controlled shading means placed between the fermentation tubes and the path of sunlight. This shading means such as an opaque hinged cover 410 as shown in FIG. 4 or adjustable screen (not shown) may be operated manually or may be regulated by computerized control temperature servo mechanical devices. Also the solar tubes may be located at different elevations or for example on the side of a hill to permit gravity to alleviate the burden of pumping the fermentation mixture through the solar tubes. The solar tubes are preferably housed within an insulated sheet metal enclosure 430 which is open on one side. The open side may be fitted with a clear plastic cover such as cover 420. The solar tubes may be arranged in a plane which can be adjusted manually by mechanical means or by servo mechanical means to maximize the exposure of the tubes to the sunlight rays.

In prior art fermentation processes for production of alcohol from grain or molasses the fermentation step is normally carried out in large closed vats resulting in a raw ethanol beer product of essentially uniform composition within the vats. The temperature of the fermentation step is conventionally regulated through the application of hot water or steam passing through external indirect heat exchangers in process communication with the fermentor vats or by electrical heating/cooling devices or fuel fired heaters connected to the fermentor. Applicant has found that the fermentation step can be carried out in situ with improved performance as the fermentation mixture is passed through the inner metal tube 35 of a conventional solar collector of the type as that disclosed in U.S. Pat. No. 4,186,725 wherein the heat required to maintain the fermenting mixture at the necessary reaction temperature is provided by sunlight energy. Thus, significant cost savings can be realized by utilizing sunlight energy to bring the fermentation mixture to reaction temperature instead of utilizing electrical heating means or other forms of external heating.

In a typical steady state operation at an ambient environmental temperature of 60° F. and at a solar heat flux rate of 330 BTU/sq. ft. per hour the fermentation mixture entering the solar tubes 35 through line 30 may be about 70° F. and the temperature at the outlet may be about 90° F. The solar fermentors 35 of the invention are operable to achieve molasses fermentation at ambient environmental temperature in a range between about 0° and 120° F. and at an average solar heat flux of between about 60 to 350 BTU/sq. ft. per hour. The fermentation step may be carried out in one long fermentation tube or preferably in a plurality of shorter tubes 35 placed in series as shown in FIG. 1. The fermentation mixture is pumped through the solar tubes 35 by conventional pumps (not shown) and/or the mixture may be aided in flow through the solar tubes by gravity if the tubes are located at different elevations. The flow rate of the fermentation mixture is adjusted to permit a residence time of 10 to 48 hours for the fermenting mixture passing through line 35. Each tube 35 is comprised of a metal inner tube of about 4 inches in diameter encased in a glass envelope of about 6 inches in diameter having an annular passage between the metal and glass tube evacuated to a pressure of about $10^{-6}$ Torr as disclosed in U.S. Pat. No. 4,186,725. The raw beer product leaving the fermentation step contains about 10 wt. % ethanol.

The raw beer product may be passed from the fermentation step through line 40 to a conventional distillation system such as that disclosed in U.S Pat. No. 3,445,345 for purification of the raw fermentation product into a highly purified 95% ethanol product which may be fit for human consumption. However, if a fuel grade ethanol for gasoline blending is desired as is the principal object of the present invention, the distillation operation need not be as rigorous as that shown in U.S. Pat. No. 3,445,345. Specifically, impurities such as fusel oil (isoamylalcohol) aldehydes, and esters present in the raw fermentation product need be fractionated from the raw product to a markedly lesser degree in production of a fuel grade alcohol product. Consequently, one or more of the distillation steps disclosed in the U.S. Pat. No. 3,445,345 can be eliminated and the distillation sequence as a whole can be simplified as herein disclosed.

In the present invention, two distillation columns 44 and 55 are utilized to produce a fuel grade 95% ethanol product. More preferably applicant has determined that significant further cost savings can be realized by supplying the reboiler heat to the distillation section through the use of solar energy instead of utilizing steam or other heating source. Therefore, in accordance with the present invention, although conventional distillation equipment can be used to purify the raw fermentation product in line 40, the preferred embodiment as disclosed in FIG. 1 utilizes a Distillation Section III which includes a two stage distillation system (columns 42 and 55) that are devoid of conventional external reboilers altogether or else are only partially dependent on use of external reboilers and nonsolar heat sources.

Figure 3:
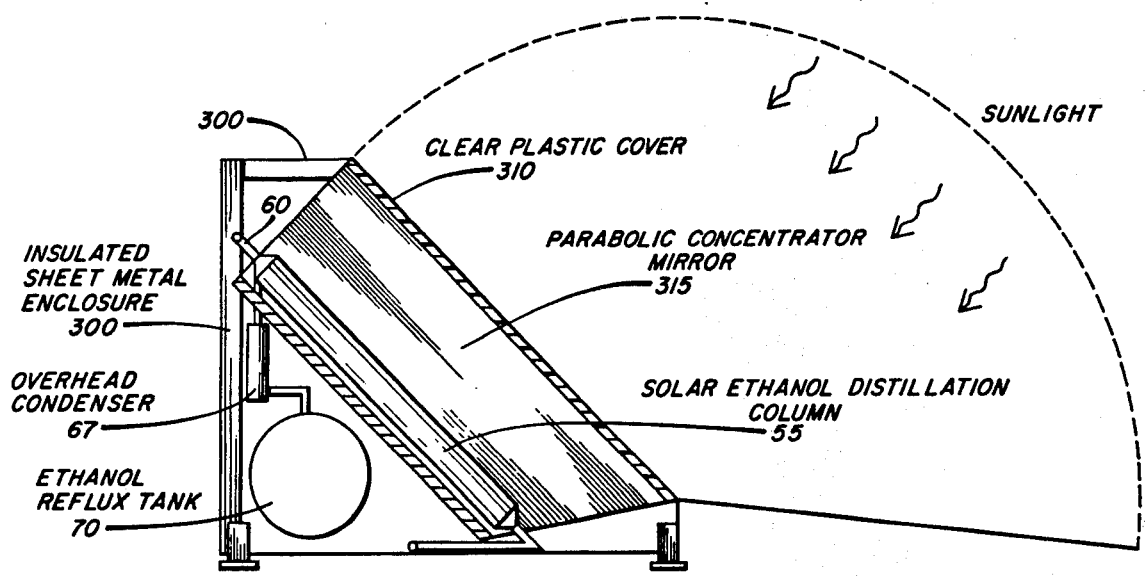
FIG. 3 is an elevational view of a distillation column.

Specifically, applicant has found that all the required reboil heat or at least a substantial portion thereof, preferably from 50% to 100%, can be supplied to each distillation column (42 and 55) by controlled exposure of the column metal surface to sunlight energy. This is accomplished preferably by orienting each distillation column 42 and 55 at a tilted angle of about 15 to 60 degrees from vertical and enclosing the column in an insulated sheet metal enclosure 300 as best shown in FIG. 3. The enclosure 300 is open at least on one side and covered on that open side by a clear polycarbonate cover plate or equivalent material located in a plane substantially parallel to the plane in which the distillation column lies as shown in FIG. 3. Additionally, parabolic reflector mirrors 315 may be included in the casing to enhance the rate of sunlight heat transfer to each column. The exposure of each distillation column to sunlight can be regulated by covering the clear cover plate 300 with the opaque material. This procedure can also be accomplished by providing computerized servomechanical control means by adjusting said opaque material over the clear cover plate. By this method, it has been found that all or at least 50% to 100% of the reboiler heat required to generate reboil vapor within each distillation column 42 and 55 for pilot scale reboiler duties from 5,000 BTU/hr to 50,000 BTU/hr or as well for commercial scale reboiler duties from 50,000 to 500,000 BTU/hr can be supplied by sunlight energy instead of employing costly steam or other external heat sources to supply the entire duty.

In accordance with the preferred embodiment the raw fermentation product is passed by conventional pumping means (not shown) from line 40 to a first stage solar reboiled ethanol column 42 which operates preferably at about 200° F. and 5 psig pressure wherein the raw fermentation stream 42 is fractionated to an overhead product stream 45 containing 75 wt. % ethanol about 18 wt. % water and no more than about 5 wt. % fusel oil (isoamylalcohol) including other impurities comprised essentially of esters and aldehydes and 2 wt. % nonvolatiles. Sufficient number of vapor-liquid perforated contacting plates are provided within the distillation column 42 to accomplish this fractionation. The distillation column 42 can be provided with reflux by passing ethanol from line 71 to the column 42.

The 75% ethanol stream is passed in line 45 to a second stage solar ethanol column 55 operating preferably at about 180° F. and 5 psig pressure wherein the ethanol is further purified to produce a 95% ethanol and fusel oil stream which is passed overhead through line 60 to an overhead condenser 67. The ethanol product is condensed in condenser 67 and passed by line 61 to an ethanol product reflux tank 70 and a portion of the condensed product is returned to column 55 as reflux. A denaturant feed tank 75 is provided to feed a denaturant such as methyl isobutyl ketone to the product tank 70 for the purpose of releasing the product from the distiller's bond.

The ethanol product produced by the proces of the invention contains 92% ethanol and the following maximum amount of impurities in weight per cent: fusel oil (isoamylalcohol) 2 wt. %; aldehydes 0.5 wt. %; water 4 wt. %; esters 0.5 wt. %; and non volatiles about 1 wt. %.

This ethanol product has sufficiently low percentage impurities and is sufficiently rich in ethanol (92% ethanol) that it can be blended with motor gasoline directly in the ratio of 1 part by weight or less ethanol product to 7 parts by weight or more gasoline to produce a fuel substitute for automobiles and other machines or the ethanol product may be used as a complete substitute for gasoline.

The bottom liquid from distillation columns 55 and 42 are comprised essentially of water and about 14 wt. % solid impurities are pumped through conventional pumping means and pass through lines 65 and 50 respectively. The streams 65 and 50 are combined in line 85 as feed to the solar evaporator column 87. The solar evaporator column 87 is a distillation column having one or more equilibrium stages. Column 87 is reboiled by the use of sunlight energy in whole or at least from 50 to 100% as in columns 42 and 55. The evaporator column 87 operates preferably at 212° F. at atmospheric pressure and has the function of boiling the water in stream 85 to produce steam and separating impurities from the stream.

The steam produced in solar evaporator 87 is passed through overhead line 90 to wash tank 95 wherein the steam is condensed by indirect heat exchange with heat reclaimation exchanger 110. The wash stillage tank 95 has the additional function of heat storage. The heat recovered by exchanger 110 is thereby available to supply heat energy to the fermentors and distillation units at night time or on days having poor sunlight. Additional heat required for night operation can be supplied by external fuel sources or steam and electricity. The bottom water from evaporator column 87 which contains approximately 50 wt. % solids is passed to storage tank 95 wherein the heat reclaimed from stream 90 is stored. The condensed steam passes from the wash tank through line 91 at about 112° F. through air cooled condenser 97 wherein it is further cooled to about 105° F. The subcooled water is then recycled through line 100 to be admixed with the incoming feed water in line 8 and the process is repeated continually.

Figure 2:
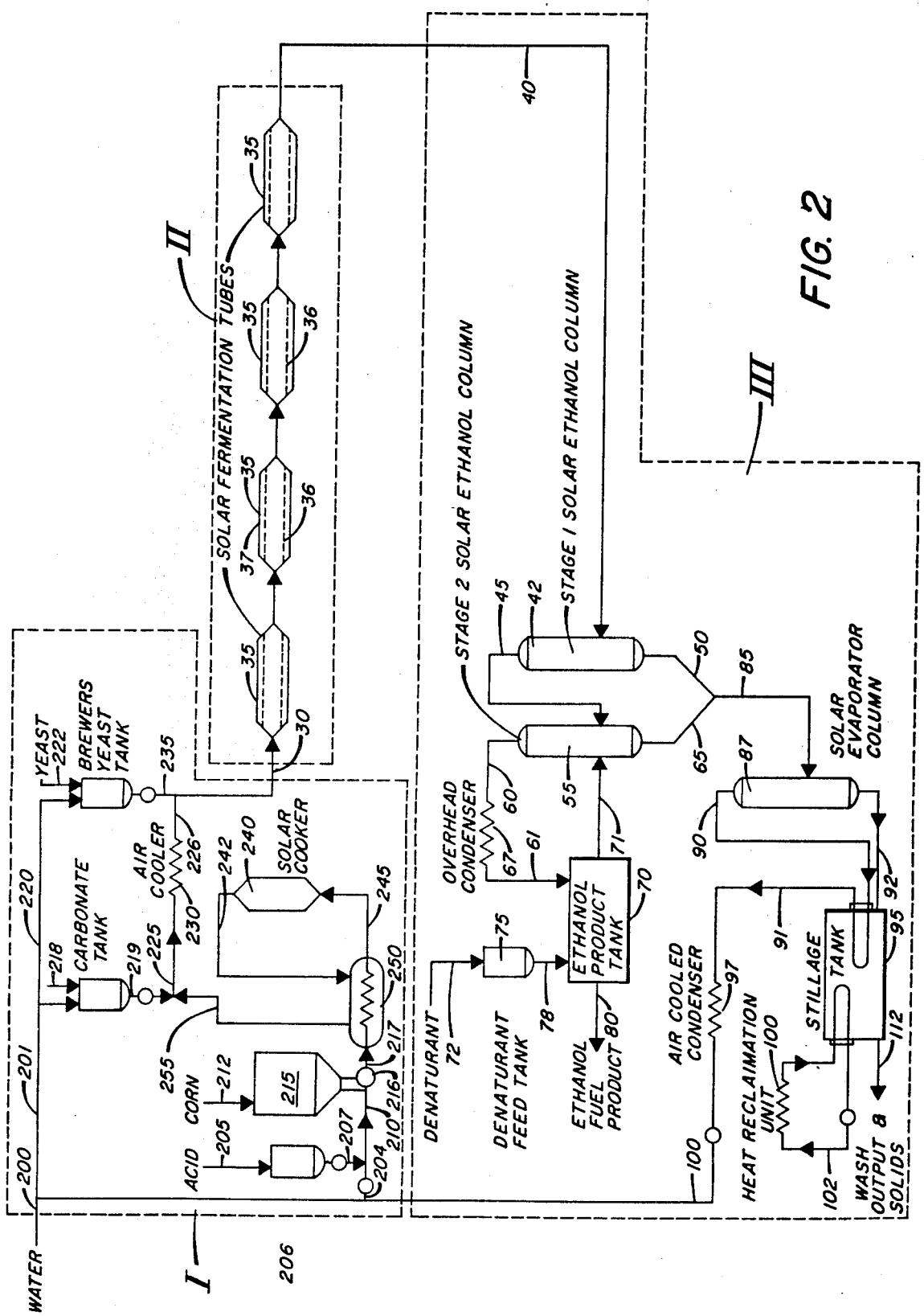
FIG. 2 is a schematic process flow diagram of another embodiment of the invention utilizing corn feed.

An alternate embodiment of this invention utilizing corn instead of molasses as feed is illustrated in FIG. 2. The process and system disclosed in FIG. 2 is comprised of a Feed Pretreatment Section IA, a Solar Fermentation Section II and a Distillation Section III. The process and system disclosed in FIG. 2 has the same preferred Solar Fermentation Section II and the same preferred Distillation Section III as shown in Figure I but the Feed Pretreatment Section IA has been modified to accommodate processing of raw corn kernals prior to the fermentation step.

Since the starch in corn cannot be digested by yeast directly it must be first hydrolized by acid, for the purpose of breaking the starch into fermentable sugars. Consequently, an acid tank 206 is provided within the Feed Pretreatment Section IA to introduce hydrosulfuric acid into the feedwater stream 204 to produce a weak acid water mixture in line 210. The acid water is mixed with the corn mash output 216 from corn mill 215. The corn mash and acid water then passes through indirect heat exchanger 250 wherein it is heated about 190° F. and then is passed to solar cooker 240 wherein it is cooked at a residence time of about 6 minutes at a temperature of about 340° F. The cooked product is passed from solar cooker 240 through line 242 to the hot side of heat exchanger 250 wherein it is cooled to about 210° F. and is then passed through line 255 to admixture with the calcium carbonate-water solution from carbonate tank 203. The added calcium carbonate serves to neutralize any free acid.

The mixture is then passed through line 225 to air cooler 230 wherein it is cooled from about 150° F. to about 90° F. The cooled feed product exits the air cooler 230 through line 266 and a solution of brewer's yeast and water is then added from yeast tank 225. The resulting mixture is then passed to the Solar Fermentation Section II and then to the Distillation Section III to produce a 95% ethanol fuel product. The preferred Solar Fermentation Section II and Distillation Section III are identical to that disclosed and described with reference to the FIG. 1 preferred embodiment.

The resulting ethanol product in line 90 is 92% ethanol having the following maximum impurities in weight per cent: fusel oil (isoamylalcohol) 2 wt. %; aldehydes 0.5 wt. %; water 4 wt. %; esters 0.5 wt. % and non volatiles 1 wt. %.

This ethanol product has sufficiently low percentage impurities and is sufficiently rich in ethanol that it may be blended with gasoline directly in the rate of 1 part by weight or less ethanol product to 7 parts by weight or more gasoline to produce a fuel substitute for automobiles and other machines, or the ethanol product may be used as a complete substitute for gasoline.

An illustrative example is set forth as follows for the following pilot scale production of ethanol utilizing the process of the invention.

EXAMPLE 1

At a steady state operation for ambient conditions at 60° F. and average solar heat flux of 330 BTU/sq. ft. per hour, 2.5 gal/hr of molasses in stream 1 was mixed with 3.75 gal/hr water in stream 2 and ½ oz/hr of 30% yeast solution in stream 3. The mixture was passed to four tubular solar fermentors in series each having an inner metal tube diameter of about 4 inches and a tube length of 40 feet. The residence time of the fermenting mixture in the solar tubes was 11 hours. The heat input rate to the fermentor tubes (augmented by parabolic reflectors) was 3360 BTU/hr and the temperature within the fermentor tubes was controlled to 90° F. The raw (beer) product leaving the fermentor tubes in line 40 contained about 10 wt. % ethanol. The raw (beer) product was distilled in the stage 1 solar ethanol column 42. The ethanol column 42 operated on about 190° F. and 2 psig pressure, and employed 20 perforated vapor liquid contacting plates. The solar heat input rate to column 42 was 6400 BTU/hr. An overhead product comprised of 75 wt. % ethanol, 5 wt. % fusel oil including aldehydes and esters (ethylacetate), 2 wt. % nonvolatiles and 18 wt. % water was removed from the column 42 overhead and passed to stage 2 ethanol column 55. The ethanol column 55 operated at about 180° F., and 2 psig pressure at a reflux ratio of 10:1 to 15:1 (varies) and employed 30 perforated vapor liquid contacting plates. The solar heat input rate to column 55 was 6400 BTU/hr.

A 95% ethanol product vapor stream was removed from the overhead line 60 of column 55 and was condensed removing 500 BTU/hr in overhead condenser 67 and then mixed with 0.5 gal/hr denaturant, e.g. methyl isobutyl ketone. An ethanol product at the rate of 1 gal/hr containing 92% ethanol resulted. The resulting 92% ethanol product contained about 3 wt. % fusel oil (isoamylalcohol) including esters and aldehydes, 1 wt. % solids and 4 wt. % water which product is suitable for blending with motor gasoline as a substitute for gasoline.

The bottoms liquid from columns 42 and 55 were combined and passed to solar evaporator column 87. The evaporator column 87 operated at 212° F. and about 2 psig. The solar input rate to column 87 was 20,000 BTU/hr. Steam at the rate of 20 lbs/hr was carried from the overhead line 90 from column 87 to indirect heat exchange in wash tank 95. The water and solids bottoms stream 92 (3 gal/hr) was passed to wash tank 95. Heat at the rate of 30,000 BTU/hr was recovered in heat reclaimation unit 102 and about 10,000 BTU/hr heat was removed in air cooled condenser 97 to condense the steam passing from the wash tank in line 91. The steam in line 91 was condensed thereby to produce about 2.5 gal/hr or water at 105° F. which was recycled to the water feed line 8. About 10,000 BTU/hr of the heat reclaimed was stored for use during the night. 1 KW hr of electricity was consumed during operation of the process. Thus the heat requirements needed in the fermentation and distillation steps were supplied entirely by solar energy except for the 1 KW hr of electricity.

A positive energy balance of 38,601 BTU's/hr resulted as follows:

| | |
|---|---|
| Total Heat Energy | 85,000 |
| Fuel Value of Ethanol Product, BTU/hr (1 gal/hr) | |
| Total Solar Heat Input  36,160 BTU/hr | |
| BTU equivalent of 1KW Electricity  10,239 BTU/hr | |
| TOTAL HEAT INPUT, BTU/hr | 46,399 |
| Positive Energy Balance, BTU/hr (Including Solar Input) | 38,601 |
| Net Positive Energy Balance (Excluding Solar Heat)* | 74,761 |

*Energy to grow, process and transport the feedstock not included.

Since sunlight heat is used instead of costly utilities, the equipment payout period from sale of the ethanol fuel product can be reduced by about 10% for the pilot plant and about 40% for large scale plants producing 1,000 lbs/hr or more of ethanol product.

EXAMPLE 2

As a steady state operation for ambient conditions at 60° F. and average solar heat flux of 330 BTU/sq. ft. per hour, 10 lbs/hr of dry shelled corn in stream 212 was mixed with 3 gal/hr of water in line 202 and 0.723 lbs/hr of 98 wt. % hydrosulfuric acid from tank 206 to form an acidized mash. The mash was preheated to 190° F. in preheater 250 and then heated to 340° F. at 150 psi in solar cooker 240. The solar heat input to the solar cooker was 4,860 BTU/hr. The cooked mash from the solar cooker was cooled to about 210° F. in preheater 250 by indirect heat exchange with the acidized feed mash in line 217. The cooled mash passed from preheater 250 through line 255 and was mixed with 3.2 gal/hr of a 5% calcium carbonate solution from line 219 to neutralize the mash. The neutralized mash was cooled to about 90° F. in air cooler 230 and then mixed with ½ oz/hr of 30% brewer's yeast water solution in line 235. The mixture was passed to four tubular solar fermentors in series each having an inner metal tube diameter of about 4 inches and tube length of 40 feet. The residence time of the fermenting mixture in the solar tubes was about 11 hours. The heat input rate to the fermentor tubes (augumented by parabolic reflectors) was 3,360 BTU/hr and the temperature within the fermentor tubes was controlled to about 90° F. The raw (beer) product leaving the fermentor tubes in line 40 contained about 10 wt. % ethanol. The raw (beer) product was distilled in the stage 1 solar ethanol column 42. The ethanol column 42 operated at about 190° F. and 2 psig pressure and employed 20 perforated vapor liquid contacting plates. The solar heat input rate to column 42 was 6,400 BTU/hr. An overhead product comprised of 75 wt. % ethanol, 4 wt. % fusel oil including aldehydes and esters, 2 wt. % non volatiles and 19 wt. % water was removed from column 42 overhead and passed to stage 2 ethanol column 55. The ethanol column 55 operated at about 180° F. and 2 psig pressure at a reflux ratio of about 10:1 to 15:1 and employed 30 perforated vapor liquid contacting plates. The solar heat input rate to column 55 was 6,400 BTU/hr.

A 95% ethanol product vapor stream was removed from the overhead line 60 of column 55 and was condensed removing 500 BTU/hr in overhead condenser 67 and then mixed with 0.05 gal/hr denaturant, e.g. methyl isobutyl ketone to produce about 1 gal/hr of ethanol product in line 80. The ethanol product contained 90% ethanol, about 2 wt. % fusel oil, about 0.5 wt. % aldehydes, 4 wt. % water, 0.5 wt. % esters and 1 wt. % nonvolatiles which product is suitable for blending with motor gasoline or as a substitute for gasoline.

The bottoms liquid from columns 42 and 55 were combined to produce 7 gal/hr of stillage feed 85 which was passed to solar evaporator 87 operating at about 212° F. and 2 psig. The evaporator column 87 reduced the water content in stillage feed line 85 from about 82% to 50%. The solar heat input rate to evaporator column 87 was about 20,000 BTU/hr. About 20 lbs/hr of steam was carried from the overhead line 90 from column 87 to indirect heat exchange in stillage tank 95. The water and solids bottoms stream 92 from the evaporator column was passed to stillage tank 95. Heat at the rate of 30,000 BTU/hr was removed in heat reclaimation unit 110 and about 10,000 BTU/hr heat was removed in air cooled condenser 97 to condense the steam passing from the wash tank in line 91. The steam in line 91 was condensed thereby to produce about 2.5 gal/hr of water at 105° F. which was recycled to the water feed line 202. About 10,000 BTU/hr of the reclaimed heat was stored for use during the night. 1 KW hr of electricity was consumed during operation of the process. Thus the heat requirements needed in the fermentation and distillation steps were supplied entirely by solar energy except for the 1 KW hr of electricity.

A positive energy balance of 33,761 BTU/hr resulted as follows:

| | | |
|---|---|---|
| Total Heat Energy | | 85,000 |
| Fuel Value of Ethanol Product, BTU/hr (1 gal/hr) | | |
| Total Solar Heat Input, BTU/hr | 41,000 | |
| BTU equivalent of 1KW electricity | 10,239 | |
| TOTAL HEAT INPUT, BTU/hr | | 51,239 |
| Positive Energy Balance, BTU/hr | | 33,761 |
| Net Positive Energy Balance (Excluding Solar Heat)* | | 74,761 |

*Energy to grow, process and transport the feedstock not included.

Since sunlight heat is used instead of costly utilities, the equipment payout period from sale of the ethanol fuel product can be reduced by about 10% for the pilot plant and about 40% for large scale plants producing 1,000 lbs/hr or more of ethanol product.

Although the foregoing example is based on a pilot scale production of ethanol it should be appreciated that the example is merely illustrative of operability of the process and that the principles and process herein disclosed can be applied as well to achieve large scale production of ethanol.

I claim:

1. A fermentation and distillation process for producing an ethanol product from an organic feed and yeast solution, the improvement comprising the steps of:
   a. entraining said solution into a continuously moving stream through a closed, elongated channel;
   b. directly applying solar energy to selected portions of said channel, whereby said solution is heated to fermentation temperature and the percentage of ethanol in said solution becomes greater as the mixture passes through said channel;
   c. passing said solution from said channel to a distillation section comprising at least one distillation column; and
   d. directly applying solar energy to said distillation column to supply from 50% to 100% of the reboil heat, said distillation column comprising a solar heat exchanger for vaporizing said solution as the feed liquid using solar energy as the heating source, said solar heat exchanger comprising:
      a closed metal boiler tube wherein vaporization of the feed liquid entering the exchanger occurs, said metal tube coated with heat absorbent coating and having an inlet opening for admitting the feed liquid into the metal boiler tube and an outlet opening for passing the vaporized product from the metal boiler tube,
      a transparent glass tube enclosing the metal tube and forming an annular space between the glass tube and the metal boiler tube, said annular space evacuated to vacuum pressure, and
      a spray tube of small diameter relative to the diameter of the metal boiler tube, said spray tube located within the metal boiler tube and having a plurality of spray orifices in close proximity to each other placed along the length of the spray tube, one end of said spray tube being in communication with said inlet opening of said metal boiler tube, said feed liquid entering said exchanger at a pressure sufficient to produce a continuous spray of said feed liquid through the spray orifices of said spray tube, said spray continuously impacting against the inside surface of said metal boiler tube to improve the rate of heat transfer to the feed liquid so that virtually all the liquid entering the metal boiler tube is converted to vapor within said metal boiler tube.

2. The process of claim 1 further comprising the steps of collecting a stream of bottom fluid from said distillation column, passing said bottom fluid to an evaporator stage, directly applying solar energy to said evaporator stage so that 75% to 100% of the energy required to vaporize said bottom fluid is provided by said solar energy, passing the resulting bottom fluid vapor into a heat exchanger to generate reclaimed heat and storing a portion of said reclaimed heat for non-solar operation.

3. The process of claim 1 wherein time duration required by said solution to pass through said channel is between 10 and 48 hours and the flow rate of said solution therethrough is substantially 0.1 to 0.5 gallons per minute.

* * * * *